(12) United States Patent
Hands

(10) Patent No.: US 6,888,359 B2
(45) Date of Patent: May 3, 2005

(54) INVESTIGATING CURRENT

(75) Inventor: Brian Hands, Seascale (GB)

(73) Assignee: British Nuclear Fuels plc, Risley (GB)

(*) Notice: Subject to any disclaimer, the term of this patent is extended or adjusted under 35 U.S.C. 154(b) by 0 days.

(21) Appl. No.: 10/221,260

(22) PCT Filed: Mar. 6, 2001

(86) PCT No.: PCT/GB01/00954
§ 371 (c)(1),
(2), (4) Date: Nov. 26, 2002

(87) PCT Pub. No.: WO01/69204
PCT Pub. Date: Sep. 20, 2001

(65) Prior Publication Data
US 2003/0184322 A1 Oct. 2, 2003

(30) Foreign Application Priority Data
Mar. 14, 2000 (GB) .............................. 0005945

(51) Int. Cl.⁷ .................. G01N 27/00; G01R 27/08
(52) U.S. Cl. ............................ 324/700; 324/71.2
(58) Field of Search .............................. 324/425, 444, 324/450, 691, 700, 71.1, 71.2; 73/623

(56) References Cited

U.S. PATENT DOCUMENTS

| | | | |
|---|---|---|---|
| 1,895,643 A | 1/1933 | Putnam | 324/176 |
| 3,853,730 A | 12/1974 | Anderson | 204/196.06 |
| 4,019,133 A | 4/1977 | Manley et al. | 324/700 |
| 4,087,749 A | 5/1978 | McCormack | 324/225 |
| 4,096,437 A | 6/1978 | Kitzlinger et al. | 324/227 |
| 4,328,462 A | 5/1982 | Jensen | 324/229 |
| 4,338,097 A | 7/1982 | Turner et al. | 436/6 |
| 4,338,563 A | 7/1982 | Rhoades et al. | 324/700 |
| 4,419,892 A | 12/1983 | Goolsby et al. | 73/865.8 |

(Continued)

FOREIGN PATENT DOCUMENTS

| | | |
|---|---|---|
| EP | 0 150 552 A1 | 8/1985 |
| EP | 0 224 230 A2 | 6/1987 |
| EP | 0 344 576 A2 | 12/1989 |
| GB | 365 555 | 1/1932 |
| WO | WO 83/03675 | 10/1983 |
| WO | WO 90/04779 | 5/1990 |
| WO | WO 94/09354 | 4/1994 |
| WO | WO 01/69223 A2 | 9/2001 |
| WO | WO 01/70003 A2 | 9/2001 |

OTHER PUBLICATIONS

Roe D. Strommen et al., *FSM–A Unique Method for Monitoring Corrosion of Steel Piping and Vessels*, N.A.C.E. Corrosion Asia Conference, Singapore, vol. 32, No. 4, Sep. 1992, pp. 50–55.

Roe D. Strommen et al., *New Technique Monitors Pipeline Corrosion, Cracking*, Oil & Gas Journal, vol. 91, No. 57, Dec. 27, 1993, pp. 88–92.

R. Strommen et al., *The FSM Technology—Operational Experience and Improvements in Local Corrosion Analysis*, Corrosion 96 The NACE International Annual Conference and Exposition, 'Online', No. 338, Mar. 24–29, 1996, pp. 1–15, XP002187991.

(Continued)

*Primary Examiner*—Vincent Q. Nguyen
(74) *Attorney, Agent, or Firm*—Workman Nydegger

(57) ABSTRACT

The invention is directed towards improved accuracy of investigations into corrosion using the methods and apparatus of the invention. In particular, the invention provides a method of investigating corrosion at a location, the method including measuring the variation in the voltage between two or more electrical contacts at a first time and at one or more other times, the two or more electrical contacts being in contact with the location, passing a current through the location at the time of the voltage measurements, providing a power source external of the location to provide an applied current, using the respective voltage values from the two or more electrical contacts in the investigation of the corrosion, the part of the applied current passing through the location being measured by the use of the Hall effect.

32 Claims, 2 Drawing Sheets

U.S. PATENT DOCUMENTS

| | | | | |
|---|---|---|---|---|
| 4,591,792 A | * | 5/1986 | Birchmeier et al. | 324/425 |
| 4,642,557 A | | 2/1987 | Ross | 324/71.2 |
| 4,703,253 A | | 10/1987 | Strommen | 324/700 |
| 4,814,702 A | * | 3/1989 | Driggers et al. | 324/225 |
| 4,821,204 A | | 4/1989 | Hüschelrath | 702/38 |
| 4,982,154 A | | 1/1991 | Schwabe et al. | 324/761 |
| 5,126,654 A | * | 6/1992 | Murphy et al. | 324/71.2 |
| 5,165,794 A | | 11/1992 | Ortiz | 374/43 |
| 5,171,517 A | | 12/1992 | Solomon et al. | 376/245 |
| 5,217,304 A | | 6/1993 | Ortiz | 374/43 |
| 5,404,104 A | * | 4/1995 | Rivola et al. | 205/776.5 |
| 5,481,198 A | | 1/1996 | Patel | 324/700 |
| 5,486,767 A | | 1/1996 | Schwabe et al. | 324/715 |
| 5,581,037 A | * | 12/1996 | Kwun et al. | 73/623 |
| 5,814,982 A | * | 9/1998 | Thompson et al. | 324/71.1 |
| 5,888,374 A | | 3/1999 | Pope et al. | 205/775.5 |
| 6,077,418 A | | 6/2000 | Iseri et al. | 205/775.5 |
| 6,680,619 B1 | | 1/2004 | Horn | 324/700 |

OTHER PUBLICATIONS

A. Daaland, *Modelling of Local Corrosion Attacks on a Plate Geometry for Developing the FSM Technology*, Insight, vol. 38, No. 12, Dec. 1996, pp. 872–875.

R. Johnson, et al., *Weld Root Corrosion Monitoring with a New Electrical Field Signature Mapping Inspection Tool*, Corrosion 2000, 'Online', Mar. 26–31, 2000, XP002187993.

M. Wang et al., *Modelling and Mapping Electrical Resistance Changes Due to Hearth Erosion in a 'Cold' Model of a Blast Furnace*, $1^{st}$ World Congress on Industrial Tomography, Apr. 14–17, 1999, pp. 161–166, XP002187994.

Roe Strommen et al., *FSM (Field Signature Method)—The New Technology for Internal Corrosion Monitoring of Pipelines, Vessels and Pressure Equipment*, Proceedings of the 1998 ASME Energy Sources Technology Conference, Houston Texas, Feb. 2–4, 1998, XP0010536.

* cited by examiner

INVESTIGATING CURRENT

BACKGROUND OF THE INVENTION

1. Field of the Invention

This invention concerns improvements in and relating to investigating current, particularly but no exclusively in relation to investigating the current actually passing through an area under going field signature method based investigations.

2. Related Technology and Summary of the Invention

The field signature method is based upon feeding a direct current through a location and measuring the electric field which is generated as a result using an array of electrical contacts on a surface of the location. Changes in the magnitude and shape of the electric field overtime can provide significant information on corrosion occurring at the location.

To make measurements an excitation current has to be applied to the location. The voltage across one or more pairs of contacts on the location to be measured and the voltage across one or more pairs of contacts on a non-corroding reference are measured repeatedly to monitor the corrosion that might be occurring.

Such a system works well in many location configurations. The present applicant has found, however, that most real life situations are unsuited for investigation using the prior art technology. Signal instability effects in those cases swamps any variation arising from the corrosion progressing. This represents a significant limitation on the applicability of such techniques.

Through investigation and detailed consideration of these real life situations the applicant has realised that only a proportion of the excitation current applied will pass through the location, with the remainder finding other paths to complete the circuit. Part of the excitation current will pass through structural supports and other such locations surrounding the location, for instance. Furthermore, the proportion of the split going through the location is very likely to vary overtime due to events having an effect on the resistance offered by the alternative routes and/or the location itself. Thus corrosion of the other routes, changes to the support structure or the like could cause variations which swamp the electric field changes caused by corrosion in the location.

The present invention aims to provide for wider applicability of field signature based techniques by identifying the source of the problem and through the provision of a method which offers a clearer picture of corrosion arising, amongst other aims.

According to a first aspect of the invention we provide a method of investigating corrosion at a location, the method including measuring the variation in the voltage between two or more electrical contacts at a first time and at one or more other times, the two or more electrical contacts being in contact with the location, passing a current through the location at the time of the voltage measurements, the current passing through the location at one or more of voltage measurements times being measured.

Preferably the method includes providing a power source external of the location to provide an applied current.

Preferably the method provides for using the respective voltage values from the two or more electrical contacts in the investigation of the corrosion.

The method may provide for the part of the applied current passing through the location being measured by the use of non-intrusive means, preferably the Hall effect. The non-intrusive means of measuring may be a bismuth spiral, a magnetically sensitive F.E.T., a rotating coil, deflection of a moveable ion vein or the use of the magnetoresistive effect.

According to a second aspect of the invention we provide a method of investigating corrosion at a location, the method including measuring the variation in the voltage between two or more electrical contacts at a first time and at one or more other times, the two or more electrical contacts being in contact with the location, passing a current through the location at the time of the voltage measurements, providing a power source external of the location to provide an applied current, using the respective voltage values from the two or more electrical contacts in the investigation of the corrosion, the part of the applied current passing through the location being measured by the use of the Hall effect.

The first and/or second aspects of the invention may involve one or more of the following features, options or possibilities.

The corrosion investigated may occur throughout the location and/or at one or more specific parts of the location. The corrosion may occur due to contact between the location and its environment. The environment in question may be the external environment for the location and/or the internal environment for the location. The corrosion may arise as a result of chemical attack on the location and/or mechanical wear on the location.

The location may be an entire article or a part there of. The location may particularly be a part of a chemical plant. The location may be a part or the whole of a pipeline, passageway, conduit, vessel, container, wall or barrier. The location may have one or more surfaces isolated from one or more other surfaces. The corrosion may effect one or more of the sets of isolated surfaces, for instance the internal surfaces in the case of a pipeline.

The variation in voltage may be an increase in voltage as corrosion progresses. The variation may occur evenly for all the respective electrical contacts considered. The variation may occur unevenly for all the respective electrical contacts considered. The variation may occur at an even rate over time. The variation may occur at an uneven rate over time. The variation may occur at an even rate around the cross-section of a pipeline or other conduit. The variation may occur at an uneven rate around the cross-section of a pipeline or other conduit.

The electrical contacts may be provided by pins or other electrically conducting elements. Preferably the electrical contacts are resiliently forced into contact with the location, for instance by springs. Ideally the electrical contacts are welded or otherwise fixed to the location. The electrical contacts may be provided in pairs, preferably with the voltage between predefined pairs being measured during the investigation. The electrical contacts and/or pairs of electrical contacts may be evenly spaced along the direction of current flow or unevenly spaced along the direction of current flow. Electrical contacts may be provided throughout the location, in the direction of current flow and/or perpendicular to the direction of current flow. The electrical contacts may be provided all around the cross-section of a pipeline or other form of conduit. The method may involve measuring the voltage for one or more pairs of electrical contacts simultaneously. Four or more and preferably eight or more pairs may be considered simultaneously. The number of pins provided may be between 8 and 256 pins, more preferably between 16 and 128 pins and ideally between 24 and 64 pins.

The electrical contacts may be provided by an electrical contact mounting unit. The mounting unit is preferably configured to match one or more surfaces of the location to be investigated. The mounting unit may be in the form of a ring, preferably a breakable ring, to investigate pipelines, conduits or other locations of circular or partially circular cross-section. The mounting unit may be in the form of a collar. Preferably all the electrical contacts are provided on a single mounting unit.

The current is preferably a DC current and particularly a square wave DC current. The DC current may be provided in a single direction but is more preferably applied in both directions, ideally alternately. The current may be applied for between 200 and 2000 ms$^{-1}$ per time and more preferably between 500 and 1000 ms$^{-1}$.

The current may be introduced to the location at one end thereof and leave at the other end thereof. The current may be introduced and/or exit by a current contact unit, preferably configured to match one or more surfaces of the location to be investigated or an element in electrical contact therewith. The current contact unit or units may be in the form of a ring, preferably a breakable ring, to investigate pipelines, conduits or other locations of circular or partially circular cross-section. The current contact unit or units may be in the form of a collar.

The voltage measurements may be made after the current has started. Preferably the voltage measurements are made at least 200 ms$^{-1}$ after the current has been applied. Preferably the voltage measurement is made within 800 ms$^{-1}$ of the current being applied. Preferably the voltage measurements are made after the current stops preferentially flowing in the surface part of the location. Preferably the voltage is steady when the voltage measurements are made.

Preferably the temperature of the two or more electrical contacts is measured at one or more of the first time and one or more other times. Preferably the temperature is measured each time a voltage is measured. Preferably the temperature of the current measuring means, for instance the non-intrusive means, is measured at one or more of the first time and one or more other times. Preferably the temperature of the current measuring means is measured at each current measurement. The temperature of the two or more electrical contacts and/or current measuring means may be measured by measuring the temperature of the electrical contacts and/or current measuring means. The temperature of the two or more electrical contacts and/or current measuring means may be measured by measuring the temperature of the location. The temperature of the two or more electrical contacts and/or current measuring means may be measured by measuring the temperature of the environment surrounding the two or more electrical contacts and/or current measuring means.

Preferably the voltage measurements are compensated for temperature variations at the electrical contacts and/or location and/or current measuring means and/or the environment(s) thereof.

The power source may be a mains power source or portable power source, such as a battery. The power source may provide the same or a different current level for respective measurements.

The current for the location at a measurement time may be used to compensate one or more voltages measured for the location or a part thereof at that measurement time for variations in the current at that measurement time compared with one or more other measurement times. Preferably the compensation is made according to the equation:

$$Fc_{Ai} = \frac{I_s}{A_s} \times \frac{A_i}{I_i} - 1 \times 1000 \text{ (parts per thousand)}$$

where
 $Fc_{Ai}$=fingerprint coefficient for a pair of electrical contacts A under investigation at time i;
 $A_s$=voltage across pair A at a reference time, preferably the start;
 $I_s$=current passing through location at the reference time, preferably the start;
 $A_i$=voltage across pair A at time i;
 $B_i$=current passing through location at the time i.

The current measurement may be made at the voltage measurement location, for instance by providing the current measuring means as part of the mounting unit. The current measuring means may be provided at a different part of the location to the part where voltage measurements are made. The current may pass through the current measuring location prior to passing through the voltage measuring location, the current measuring location being provided between the closest potential current leakage route and the voltage measuring location considered in the direction of current flow. The current may pass through the voltage measuring location prior to passing through the current measuring location, the current measuring location being provided between the voltage measuring location and the closest potential current leakage route considered in the direction of current flow.

The Hall effect may be measured to measure the current passing though the location. The Hall effect measurement may be taken to be proportional to the current passing, preferably linearly proportional to the current passing through the location. The Hall effect may be measured by providing a semi-conductor material and applying a constant current through it in a first direction. The first direction is preferably configured to be substantially, and ideally to be, perpendicular to the direction of the magnetic field, the second direction, generated by the current passing through the location. The Hall effect may be measured by measuring the Hall voltage. The Hall effect may be measured by measuring a voltage arising across the semi-conductor, preferably substantially perpendicular to the first and the second direction and ideally perpendicular to both directions.

The Hall effect may be measured using a Hall effect transducer.

The Hall effect transducer may be configured to match one or more surfaces of the location. The Hall effect transducer may be in the form of a ring, preferably a breakable ring, to investigate pipelines, conduits or other locations of circular or partially circular cross-section. The Hall effect transducer may be in the form of a collar. The Hall effect transducer is preferably provided in proximity with the location. The Hall effect transducer is preferably electrically isolated from the current passing through the location.

The Hall effect transducer may include a semi-conductor material and ferromagnetic material, the ferromagnetic material being provided between at least part of the semi-conductor material and the location. Preferably an air gap is provided between the ferromagnetic material and the surface of the location. A material for reflecting thermal radiation may be provided between the ferromagnetic material and the location, for instance a reflective foil. The ferromagnetic material may be of the ferrite Mn—Zn variety or of the ferrite Si—Fe variety.

The measurements made by the Hall effect transducer may be corrected for variations in temperature. A temperature sensor in proximity with the Hall effect transducer may be used to effect the temperature correction, for instance via a feedback circuit which is used to maintain the drive current to the Hall effect transducer at a value which nullifies variations in temperature over time.

The Hall effect transducer, and particularly the semiconductor material thereof, may be shielded against radiation, particularly radiation arising within the location being considered. High density materials such as tungsten, lead, depleted uranium or other heavy alloys may be used for this purpose.

Preferably the current is measured by use of the Hall effect at substantially the same time, and ideally at the same time, as one or more of the voltage measurements are made. Preferably the current is measured by use of the Hall effect whenever a voltage measurement is made. The current may be measured when the voltage between the electrical contacts being considered is stable and/or constant. Preferably the current measurement is made at least 200 ms$^{-1}$ after the current has been applied. Preferably the current measurement is made within 800 ms$^{-1}$ of the current being applied. Preferably the current measurements are made after the current stops preferentially flowing in the surface part of the location.

The method preferably includes compensating voltage measurements at one or more times relative to voltage measurements at one or more other times according to any variation in the proportion of the applied current which passes through the location at different times of investigation.

According to a third aspect of the invention we provide apparatus for investigating corrosion at a location, the apparatus including two or more electrical contacts in contact with the location in use, means for measuring the variation in the voltage between the two or more electrical contacts, at a first time and at one or more other times, a power source for passing a current through the location at the time of the voltage measurements, current measuring means for the current passing through the location at one or more of the voltage measurements times, the current measuring means being non-intrusive.

According to a fourth aspect of the invention we provide apparatus for investigating corrosion at a location, the apparatus including two or more electrical contacts in contact with the location in use, means for measuring the variation in the voltage between the two or more electrical contacts at a first time and at one or more other times, a power source to provide an applied current, means for passing a current through the location at the time of the voltage measurements, passing the applied current through a reference location and measuring the variation in the voltage between two or more reference electrical contacts at the first time and at one or more of the one or more other times, the two or more reference electrical contacts being in contact with the reference location, using the respective voltage values from the two or more electrical contacts and two or more reference electrical contacts in the investigation of the corrosion, the part of the applied current passing through the location being measured by the use of the Hall effect.

The third and/or fourth aspects of the invention may include any of the features, options or possibilities set out elsewhere in this document, including means to implement them.

The electrical contacts may be provided by an electrical contact mounting unit. A mounting unit is preferably configured to match one or more surfaces of the location to be investigated. The mounting unit may be in the form of a ring, preferably a breakable ring. The mounting unit may be in the form of a partial ring. The mounting unit may be in the form of a collar.

The electrical contact may be provided by pins or other electrically conducting elements, preferably mounted on the mounting unit. Preferably the electrical contacts are resiliently biased, ideally towards the location in use. The electrical contact may be biased by springs. The electrical contacts are preferably provided in pairs. The electrical contact and/or pairs of electrical contacts may be evenly spaced along the mounting unit.

Preferably the current is introduced by an external power source. A mains power source or portable power source, such as a battery, may be used.

The apparatus may include beams for introducing the current to one part of the location and removing the current from another part of the location. The means may comprise a current contact unit, preferably configured to match one or more surfaces of the location to be investigated and/or an element in electrical contact with one or more surfaces of the location to be investigated. The current contact unit or units may be in the form of a ring, preferably a breakable ring. The current contact unit or units may be in the form of a partial ring and/or collar.

The non-intrusive current measuring means may be configured to match one or more surfaces of the location. The non-intrusive current measuring means may be in the form of a ring, preferably a breakable ring. The non-intrusive current measuring means may be in the form of a collar and/or partial ring.

The Hall effect current measuring means may be provided by a semi-conductor material with an applied constant current passing through it in a first direction. The first direction is preferably configured to be substantially, and ideally to be, perpendicular to the direction of the magnetic field, the second direction, generated by the current passing through the location. The Hall effect may be measured by measuring the Hall voltage. The Hall effect may be measured by measuring a voltage arising across the semiconductor, preferably substantially perpendicular to the first and second direction, ideally perpendicular to both directions. The Hall effect current measuring means may be one or more Hall effect transducers.

BRIEF DESCRIPTION OF THE DRAWINGS

Various embodiments of the invention will now be described, by way of example only, with reference to the accompanying drawings in which.

DETAILED DESCRIPTION OF THE INVENTION

It is desirable to be able to monitor corrosion and/or erosion of the materials in a non-destructive, non-intrusive manner. To be successful the technique must be capable of operating accurately within a temperature range of 10° C. to 110° C. or potentially even higher. Additionally, the system must be capable of operating in environments exposed to or containing radiation and in situations where the electrical conductivity of the contents of the location, primarily pipes, may vary with time.

When ever an electric current is passed through a location an electric field is generated. The material, thickness of material, shape and configuration of the location effect the size and shape of the electric field that results. Changes in one or more of these potential variables effects the electric field. In particular, corrosion of a location, such as a pipeline, generally reduces the thickness of material, increases the resistance and hence the voltage drop between different positions along the location in the direction of current flow.

The field effect method makes use of this basic principal to provide information on corrosion. The method applies an excitation current to the location under consideration for a short time period, fractions of a second, and measures the voltage drops between a large number of different pairs of electrical contacts touching the location. By considering the results the progress of corrosion can be evaluated. In general the results are considered in terms of a fingerprint coefficient for a given pair of electrical contacts with time. A reference pair of electrodes is provided on a non-corroding material through which the excitation current passes on its way to the location. This feature is generally employed so that variations between measurement in the current provided by the power supply do not effect the measurements.

The temperature of the reference pair of electrodes and different pairs of electrical contacts touching the location is measured so as to correct for any variation in temperature between measurement times and the effect that temperature variation would have on the signals arising.

Information on general corrosion due to a general variation in the field over time can be investigated and monitored and/or localised corrosion can be investigated and monitored where variations occur for only some of the pairs of electrical contacts.

In some real life situations the technique has been found not to work as the variations in the signals are not consistent with the corrosion anticipated and checked through other means.

Figure 1:
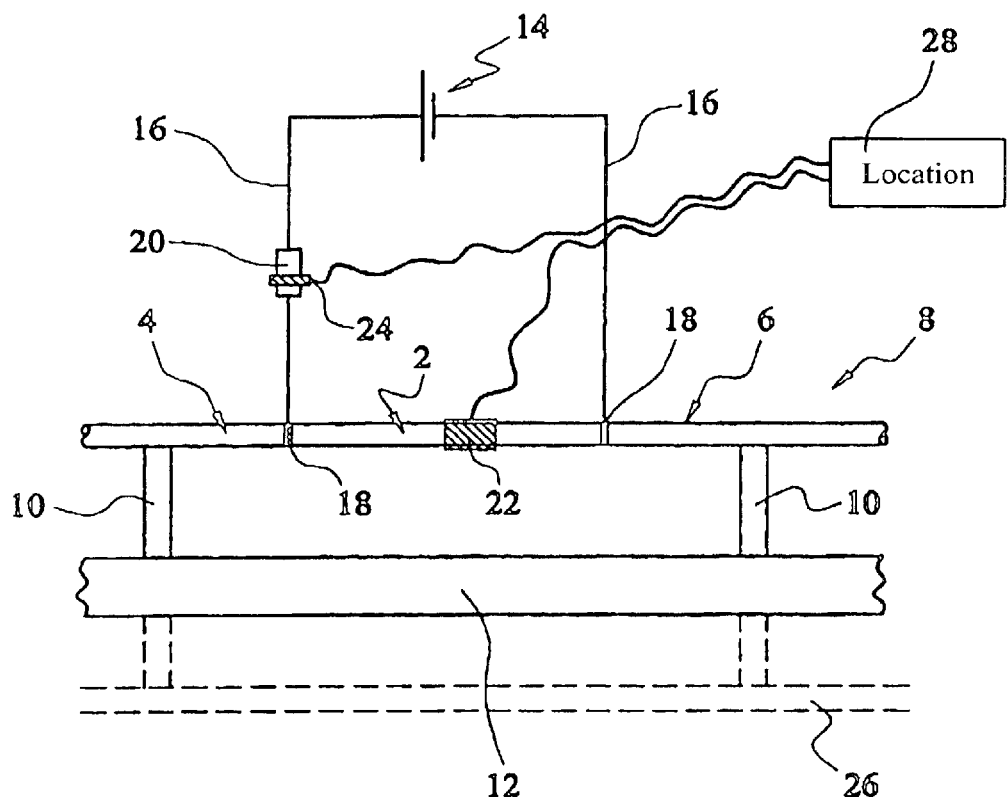
FIG. 1 illustrates schematically a location for investigation using field signature based techniques, and surrounding elements.

The applicant has established that the problem arises due to the issues now discussed in more detail. As illustrated in FIG. 1, the location 2 under consideration may be a section of pipeline between two other sections, 4 and 6 respectively, which form the general pipeline 8. The pipeline 8 is provided with support at two locations 10 in the portion shown in FIG. 1 the support locations 10 themselves being joined together by the metal frame work 12 which supports the pipeline 8 and other parts of the process plant.

The field signature method based apparatus is generally introduced when a plant is constructed and includes a power source 14 for applying the excitation current, electrical connectors 16 leading to collars 18 which introduce the current to the location 2 and a reference material 20 (which is non-corroding in the environment it is placed in) being provided between the power source 14 and collar 16. An array of electrical contacts are attached to the location 2 in electrical contact there with by measurement assembly 22 and at least one pair of electrical contacts is provided on the reference material 20 by reference measurement assembly 24. Voltage signals from the measurement assembly 20 and reference assembly 24 are collected by wires and processed at location 28 to give the desired information on corrosion over time.

The non-functioning of prior art systems has been determined by the applicant to stem from the fact that whilst all the excitation current passes through the reference material 20 in such cases and hence contributes to the measurements made by the reference measurement assembly 24, only a proportion of the excitation current passes through location 2, with the remainder of the current passing through the pipeline portion 4 to support location 10, general support frame 12, other support location 10 and pipeline portion 6 before returning to the power source 14.

As the proportion of the current taking these two paths, and potentially many more is not known potential errors are introduced. This is particularly so as the proportion following the route of interest through the location 2 may change over time, again in an unknown manner, as the respective resistances of the paths change due to corrosion, which could be at different rates, and/or due to other events which effect the resistance, for instance a modification to the plant which lays a new pipeline 26 parallel to the first 8 and forms a new current path.

The variations in the electric field which arise through these events have been established by the applicant to be the source of the swamping of the very small changes which field signature techniques seek to measured and attributed to corrosion. This is problem with the prior art is particularly applicable to general corrosion measurements.

Figure 2:
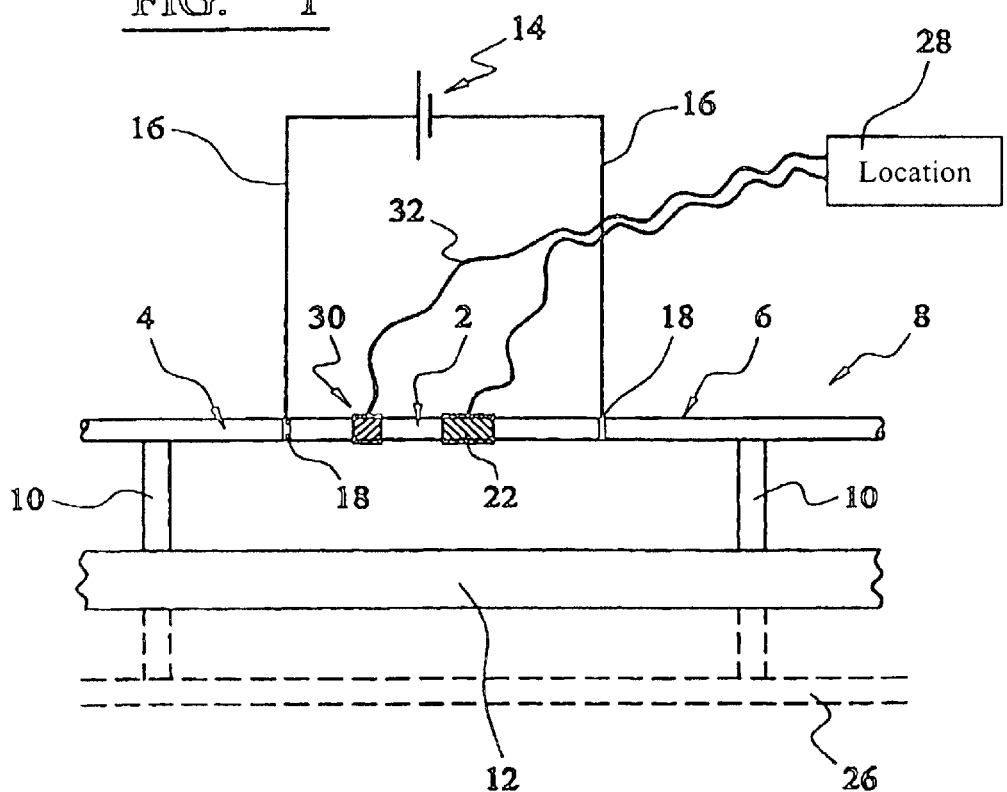
FIG. 2 illustrates a modified investigation according to the present invention.

To counteract this problem area the applicant has determined that it is imperative to measure the actual current passing through the location 2. The present invention thus provides a method and apparatus, FIG. 2, which allows the actual current passing through the location 2 to be measured as corrosion investigating measurements are made.

To achieve this the invention deploys a current measuring system 30 for the location 2 in question. The current readings are fed by wires 32 to be processing location 28 so that the voltage measurements can be compensated.

Compensation of the expression of the corrosion progress for one or more pairs of electrical contacts may be provided by the formula:

$$Fc_{Ai} = \frac{I_s}{A_s} \times \frac{A_i}{I_i} - 1 \times 1000 \text{ (parts per thousand)}$$

where $Fc_{Ai}$=fingerprint coefficient for electrode pair A at time i;
$A_s$=voltage across pair A at start;
$I_s$=current passing through location at start;
$A_i$=voltage across pair A at time i; and
$I_i$=current passing through location at time i.

The current measurement system is provided at the measurement position for the location or within the location between the measurement position and the closest potential current leakage route on that side of the measurement position. The type of current measurement used, however, has also been deemed to be important. The variations in electric field which are being measured are very small and, particularly for location specific corrosion consideration, may occur over a very small area. The system used must therefore have no interfering or altering effect on the electric field passing through the location. Additionally as the excitation current is only present for a short time, fraction of a second, the system must be capable of responding in time to measure the actual current passing. Clearly the actual current must also be very accurately measured.

The preferred form of the invention uses a Hall effect transducer to achieve the actual current measurement for the location.

Figure 3:
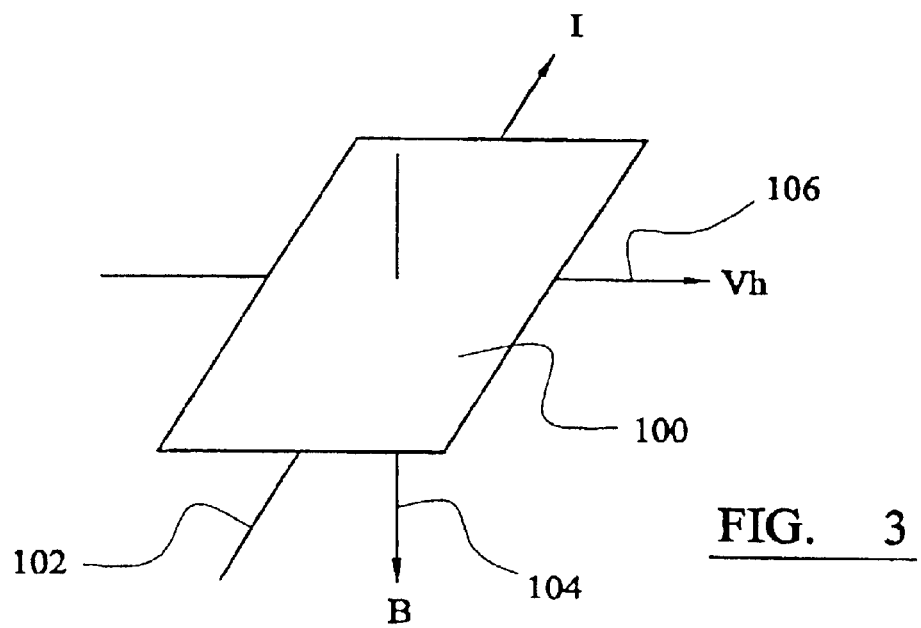
FIG. 3 illustrates the principle of the Hall effect.

In general Hall effect transducers use the magnetic field generated by a flowing current to determine that current. As illustrated in FIG. 3, the transducer uses a semi-conductor material 100 through which a constant current 102 flows perpendicular to the magnetic field 104 generated by the current to be measured. This situation results in the Hall effect voltage 106 being seen across the semi-conductor 100 and this voltage 106 is linearly proportional to the magnetic field 104 and hence the current to be measured.

A transducer using the Hall effect is suited to accurate measurement of the actual current of interest to the required degree of accuracy and to do so without effecting the actual current level or path in any way.

Figure 4:
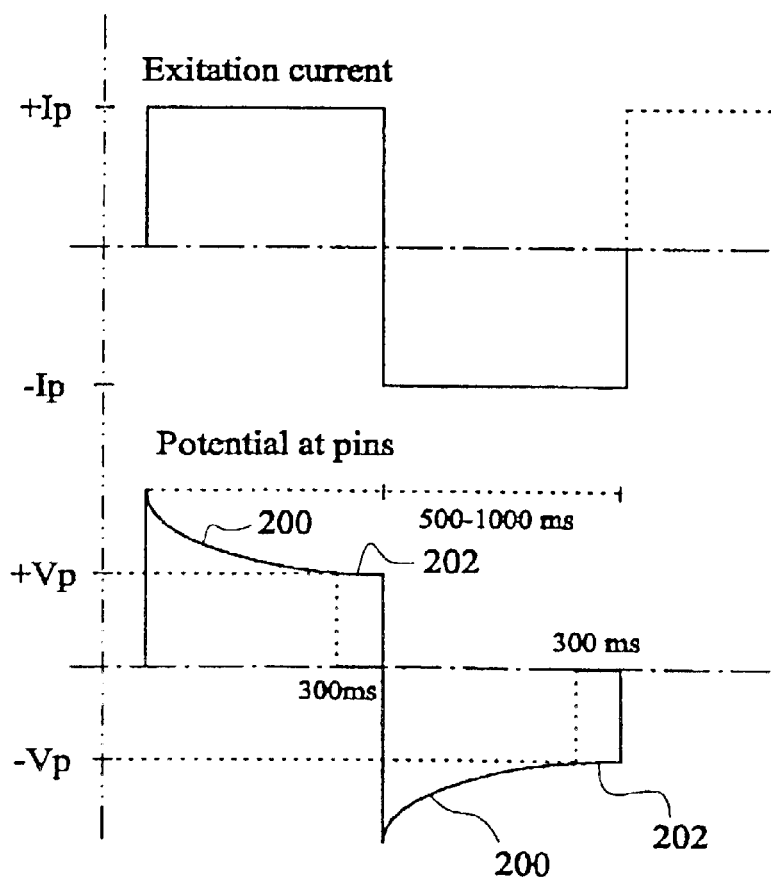
FIG. 4 illustrates the excitation current and pin potential with time for an investigation method.

As shown in FIG. 4 the type of direct excitation currents used in field signature methods also has a bearing on the technique used. The excitation current, upper curve of FIG. 4, is generally applied in a square wave form in alternating directions. The nature of the locations, and particularly surface effects of the location, mean that it initially behaves as an AC signal in each cycle, portion 200 in FIG. 4, with a preference to flow in the skin. This portion 200 of the signal ends as the signal stabilises after a time and a portion 202 occurs providing a true measure of the voltage occurs. In general current is applied in a given direction for around 1000 ms$^{-1}$ before being reversed and the stable signal portion represents the last 300 ms$^{-1}$ or so of this. Thus the current measurement technique must be quick enough to fit into this time frame and must respond quickly enough to account for the current and voltage stabilising to the part that is measured.

This situation ties in well with the practical position for the Hall effect as to measure the current passing a similar time period is needed for the Hall effect to build up after the current switches. Thus the timing of measurement coincides well.

The Hall effect has also been established to work well despite any surface effects and despite any protective or insulating material around the pipe or other location being considered. Hall effect transducers can also readily be made to encompass a variety of location cross-sections and so avoid any problems from the actual current following an uneven flow cross-section through the location.

The ability to form Hall effect transducers in the form of rings which can be broken to install them also means that the system is suitable for introduction to locations which are continuously joined to other elements as the ring can be broken, wrapped around and then reformed at the location.

Experimental evaluation of the use of Hall effect transducers in such situations has confirmed that they are capable of handling the range of temperature variation encountered, for instance from −5° C. through to 125° C. without detrimental effect on the accuracy of the results, particularly where temperature variation compensation is provided. Additionally, it has been established that the Hall effect transducers can operate successfully even in radiation containing environments, with shielding where necessary.

Furthermore, even with a location such as a pipe carrying concentrated nitric acid, the relative electrical conductivity of the liquid compared with the pipe is such that less than 0.01% of the current passes through the liquid with the remainder flowing through the location.

What is claimed is:

1. A method of investigating corrosion at a location, the method comprising:

measuring the variation in the voltage between two or more electrical contacts at a first time and at one or more other times, the two or more electrical contacts being in contact with the location;

passing a current through the location at the time of the voltage measurements;

using the respective voltage values from the two or more electrical contacts in the investigation of corrosion; and the part of the applied current passing through the location at one or more of the voltage measurements at the times being measured.

2. A method according to claim 1 in which the current is measured by non-intrusive means.

3. A method according to claim 1 wherein the part of the applied current passing through the location being measured is measured by the use of the Hall effect.

4. A method according to claim 1 wherein the part of the applied current passing through the location being measured is measured by the use of one or more of a minimum spiral, a magnetic sensitive F.E.T., a rotating coil, deflection of a moveable ion vane or the use of the magneto-resistive effect.

5. A method according to claim 1 in which the current for the location at a measurement time is used to compensate one or more voltages measured for the location or a part thereof at that measurement time for variations in the current at that measurement time compared with one or more other measurement times.

6. A method according to claim 5 in which the compensation is made according to the equation:

$$Fc_{Ai} = \frac{I_s}{I_i} \times \frac{A_i}{A_s} - 1 \times 1000 \text{ (parts per thousand)}$$

where $Fc_{Ai}$=fingerprint coefficient for a pair of electrical contacts A under investigation at time i;

$A_s$=voltage across pair A at a reference time, preferably the start;

$I_s$=current passing through location at the reference time, preferably the start;

$A_i$=voltage across pair A at time i; and $I_i$=current passing through location at the time i.

7. A method according to claim 1 in which the current is measured by use of the Hall effect at substantially the same time as the voltage measurements are made.

8. A method according to claim 1 in which the current passes through the current measuring location prior to passing through the voltage measuring location, the current measuring location being provided between the closest potential current leakage route, and the voltage measuring location considered in the direction of current flow.

9. A method according to claim 1 in which the current passes through the voltage measuring location prior to passing through the current measuring location, the current measuring location being provided between the voltage measuring location and the closest potential leakage route considered in the direction of current flow.

10. A method according to claim 3 in which current measurements made by a Hall effect transducer are corrected for variations in temperature.

11. A method according to claim 10 in which the temperature sensor in proximity with the Hall effect transducer is used to affect the temperature correction via a feedback circuit which is used to maintain the drive current and the Hall effect transducer at a value which nullifies variations in temperature over time.

12. A method according to claim 3 in which a Hall effect transducer is provided and is shielded against radiation.

13. A method according to claim 3 in which the current is measured by the use of the Hall effect and the current measurement is made at least 200 $ms^{-1}$ after the current has been applied, and the current measurement is made within 800 $ms^{-1}$ of the current being applied.

14. Apparatus for investigating corrosion at a location, the apparatus comprising:

two or more electrical contacts in contact with the location in use;

means for measuring the variation in the voltage between the two or more electrical contacts at a first time and at one or more other times using the respective voltage values from the two or more electrical contacts in the investigation of the corrosion;

a power source to provide an applied current;

means for passing a current through the location at the time of the voltage measurements; and the part of the applied current passing through the location being measured.

15. Apparatus according to claim 14 in which the current is measured by means using the Hall effect.

16. Apparatus according to claim 15 in which the Hall effect is measured using a Hall effect transducer and the Hall effect transducer is configured to match one or more surfaces of the location.

17. Apparatus according to claim 16 in which the Hall effect transducer is in the form of a ring.

18. Apparatus according to claim 17 in which the ring is breakable.

19. Apparatus according to claim 16 in which material for reflecting thermal radiation is provided between ferromagnetic material and the Hall effect transducer and the location.

20. A method of measuring the progress of corrosion at a location, the method comprising:

measuring the variation in the voltage between two or more electrical contacts at a first time and at one or more other times, the two or more electrical contacts being in contact with the location;

passing a current through the location at the time of the voltage measurements;

using the respective voltage values from the two or more electrical contacts in the measurement of the progression of corrosion; and the part of the applied current passing through the location at one or more of the voltage measurements at the times being measured.

21. A method according to claim 20 in which the current is measured by non-intrusive means.

22. A method according to claim 20 wherein the part of the applied current passing through the location being measured is measured by the use of the Hall effect.

23. A method according to claim 20 wherein the part of the applied current passing through the location being measured is measured by the use of one or more of a minimum spiral, a magnetic sensitive F.E.T., a rotating coil, deflection of a moveable ion vane or the use of the magneto-resistive effect.

24. A method according to claim 20 in which the current passes through the current measuring location prior to passing through the voltage measuring location, the current measuring location being provided between the closest potential current leakage route, and the voltage measuring location considered in the direction of current flow.

25. A method according to claim 20 in which the current passes through the voltage measuring location prior to passing through the current measuring location, the current measuring location being provided between the voltage measuring location and the closest potential leakage route considered in the direction of current flow.

26. Apparatus for measuring the progress of corrosion at a location, the apparatus comprising:

two or more electrical contacts in contact with the location in use;

means for measuring the variation in the voltage between the two or more electrical contacts at a first time and at one or more other times;

using the respective voltage values from the two or more electrical contacts in the measurement of the progress of corrosion;

a power source to provide an applied current;

means for passing a current through the location at the time of the voltage measurements; and the part of the applied current passing through the location being measured.

27. Apparatus according to claim 26 in which the Hall effect is measured using a Hall effect transducer and the Hall effect transducer is configured to match one or more surfaces of the location.

28. Apparatus according to claim 26 in which material for reflecting thermal radiation is provided between ferromagnetic material and the Hall effect transducer and the location.

29. A method of investigating corrosion at a location, the method comprising:

measuring the variation in the voltage between two or more electrical contacts at a first time and at one or more other times, the two or more electrical contacts being in contact with the location;

passing a current through the location at the time of the voltage measurements;

using the respective voltage values from the two or more electrical contacts in the investigation of corrosion;

the part of the applied current passing through the location at one or more of the voltage measurements at the times being measured;

the current for the location at a measurement time being used to compensate one or more voltages measured for the location or a part thereof at that measurement time for variations in the current at that measurement time compared with one or more other measurement times;

the compensation being made according to the equation:

$$Fc_{Ai} = \frac{I_s}{I_i} \times \frac{A_i}{A_s} - 1 \times 1000 \text{ (parts per thousand)}$$

where $Fc_{Ai}$=fingerprint coefficient for a pair of electrical contacts A under investigation at time i;

$A_s$=voltage across pair A at a reference time, preferably the start;

$I_s$=current passing through location at the reference time, preferably the start;

$A_i$=voltage across pair A at time i; and $I_i$=current passing through location at the time i.

30. A method of investigating corrosion at a location, the method comprising:

measuring the variation in the voltage between two or more electrical contacts at a first time and at one or more other times, the two or more electrical contacts being in contact with the location;

passing a current through the location at the time of the voltage measurements;

using the respective voltage values from the two or more electrical contacts in the investigation of corrosion;

the part of the applied current passing through the location at one or more of the voltage measurements at the times being measured, wherein the part of the applied current passing through the location being measured is measured by the use of the Hall effect;

the current measurements made by a Hall effect transducer are corrected for variations in temperature; and a temperature sensor in proximity with the Hall effect transducer being used to affect the temperature correction via a feedback circuit which is used to maintain drive current and the Hall effect transducer at a value which nullifies variations in temperature over time.

31. A method of investigating corrosion at a location, the method comprising:

measuring the variation in the voltage between two or more electrical contacts at a first time and at one or more other times, the two or more electrical contacts being in contact with the location;

passing a current through the location at the time of the voltage measurements;

using the respective voltage values from the two or more electrical contacts in the investigation of corrosion;

the part of the applied current passing through the location at one or more of the voltage measurements at the times being measured;

the part of the applied current passing through the location being measured is measured by the use of the Hall effect; and the current measurement being made at least 200 $ms^{-1}$ after the current has been applied, and the current measurement being made within 800 $ms^{-1}$ of the current being applied.

32. Apparatus for investigating corrosion at a location, the apparatus comprising:

two or more electrical contacts in contact with the location in use;

means for measuring the variation in the voltage between the two or more electrical contacts at a first time and at one or more other times;

means for using the respective voltage values from the two or more electrical contacts in the investigation of the corrosion;

a power source to provide an applied current;

means for passing a current through the location at the time of the voltage measurements; and the part of the applied current passing through the location being measured using the Hall effect, the Hall effect being measured using a material for reflecting thermal radiation which is provided between a ferro-magnetic material and a Hall effect transducer and the location.

* * * * *

UNITED STATES PATENT AND TRADEMARK OFFICE
CERTIFICATE OF CORRECTION

PATENT NO. : 6,888,359 B2  Page 1 of 1
DATED : May 3, 2005
INVENTOR(S) : Brian Hands It is certified that error appears in the above-identified patent and that said Letters Patent is hereby corrected as shown below:

Title page,
Item [56], References Cited, OTHER PUBLICATIONS, "Roe Strommen et al.," reference, change "XP0010536" to -- XP00105536 --.

Column 1,
Line 14, after "result" insert -- of --.
Line 19, after "make measurements" insert -- , --.
Lines 28-29, "effects in those cases swamps" to -- effects, in those cases, swamp --.
Line 33, after "real life situations" insert -- , --.
Line 54, after "including" insert -- : --.
Line 62, change "measurements" to -- measurement --.

Column 9,
Line 35, after "In general" insert -- , --.

Signed and Sealed this

Twentieth Day of September, 2005

JON W. DUDAS
*Director of the United States Patent and Trademark Office*